(12) United States Patent
Hirasawa et al.

(10) Patent No.: US 8,993,282 B2
(45) Date of Patent: Mar. 31, 2015

(54) CAROTENOID FERMENTATION METHOD

(75) Inventors: Kazuaki Hirasawa, Kanagawa (JP);
Akira Tsubokura, Kanagawa (JP);
Hiroshi Satou, Kanagawa (JP);
Tetsuhisa Yata, Kanagawa (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 54 days.

(21) Appl. No.: 13/124,304

(22) PCT Filed: Oct. 16, 2009

(86) PCT No.: PCT/JP2009/067935
§ 371 (c)(1),
(2), (4) Date: Jul. 1, 2011

(87) PCT Pub. No.: WO2010/044469
PCT Pub. Date: Apr. 22, 2010

(65) Prior Publication Data
US 2011/0262981 A1      Oct. 27, 2011

(30) Foreign Application Priority Data
Oct. 17, 2008   (JP) ................ 2008-268106

(51) Int. Cl.
C12P 7/26 (2006.01)
C12P 7/02 (2006.01)
C12P 5/00 (2006.01)
C12P 5/02 (2006.01)
C12P 23/00 (2006.01)
C07C 45/00 (2006.01)
C07C 35/21 (2006.01)
C12R 1/01 (2006.01)

(52) U.S. Cl.
CPC .. *C12P 23/00* (2013.01); *C12R 1/01* (2013.01)
USPC ........... 435/148; 435/155; 435/166; 435/167; 435/67; 568/324; 568/816

(58) Field of Classification Search
USPC ........... 435/148, 155, 166, 167, 67; 568/324, 568/816
See application file for complete search history.

(56) References Cited

U.S. PATENT DOCUMENTS

| | | | |
|---|---|---|---|
| 5,607,839 A | 3/1997 | Tsubokura et al. | |
| 5,935,808 A | 8/1999 | Hirschberg et al. | |
| 5,962,756 A | 10/1999 | Koch et al. | |
| 7,745,170 B2 * | 6/2010 | Tsubokura et al. | 435/67 |
| 8,097,761 B2 * | 1/2012 | Ishizaki et al. | 568/345 |
| 2006/0121556 A1 | 6/2006 | Hirasawa et al. | |
| 2007/0054351 A1 | 3/2007 | Zhang | |
| 2007/0105189 A1 | 5/2007 | Tsubokura et al. | |
| 2009/0221026 A1 | 9/2009 | Tanaka et al. | |
| 2009/0298146 A1 | 12/2009 | Choi et al. | |
| 2010/0285524 A1 | 11/2010 | Tanaka et al. | |

FOREIGN PATENT DOCUMENTS

| | | | | |
|---|---|---|---|---|
| CN | 1875112 A | 12/2006 | | |
| EP | 0 635 576 A1 | 1/1995 | | |
| EP | 1229126 A1 | 8/2002 | | |
| EP | 1496115 A1 | 1/2005 | | |
| EP | 2157169 A1 | 2/2010 | | |
| EP | 2345736 A1 | 7/2011 | | |
| JP | 54-24940 A | 2/1979 | | |
| JP | 05-276989 | * 10/1993 | ............. | C12P 23/00 |
| JP | 05-276989 A | 10/1993 | | |
| JP | 7-79796 A | 3/1995 | | |
| JP | 11-69969 A | 3/1999 | | |
| JP | 11-513707 A | 11/1999 | | |
| JP | 2001-512030 A | 8/2001 | | |
| JP | 2005-046027 A | * 2/2005 | ............. | C12P 23/00 |
| JP | 2005-46027 A | 2/2005 | | |
| JP | 2005-87099 A | 4/2005 | | |
| JP | 2005-087100 A | 4/2005 | | |
| JP | 2006-191919 A | 7/2006 | | |
| JP | 2006-340676 A | 12/2006 | | |
| JP | 2007-97584 A | 4/2007 | | |
| JP | 2007-143492 A | 6/2007 | | |
| JP | 2007-244205 A | 9/2007 | | |
| JP | 2008-167665 A | 7/2008 | | |
| JP | 2008-259452 A | 10/2008 | | |
| NZ | 563130 A | 4/2010 | | |
| WO | 88/08025 A1 | 10/1988 | | |
| WO | 94/23057 A1 | 10/1994 | | |
| WO | 97/15554 A1 | 5/1997 | | |

(Continued)

OTHER PUBLICATIONS

Alper et al., Characterization of lycopene-overproducing *E.coli* strains in high cell density fermentations. Appl Microbiol Biotechnol., 2006, vol. 72: 968-974.*
Kim et al., *Paracoccus homiensis* sp. nov., isolated from a sea-sand sample. Int. J. System. Evol. Biol., 2006, vol. 56: 2387-2390.*
Pukall et al., *Paraoccus seriniphilus* sp. nov., an L-serine-dehydratase-producing coccus isolated from marine bryozoan *Buglua plumosa*. Int. J. System. Evol. Biol., 2003, vol. 53: 443-447.*
S. Alcantara, et al., Influence of carbon and nitrogen sources on Flavobacterium growth and zeaxanthin biosynthesis, Journal of Industrial Microbiology & Biotechnology, vol. 23, No. 1, pp. 697-700, 1999.
E. Widmer, Synthetic advances in the carotenoid field, Pure & Appl. Chem., vol. 57, No. 5, pp. 741-752, 1985.
E. Widmer, et al., Technische Verfahren zur Synthese von Carotinoiden und verwandten Verbindungen aus 6-Oxo-isophoron. II. Ein neues Konzept fur die Synthese von (3RS,3'RS)-Astaxanthin1)2), Helvetica Chimica Acta, vol. 64, pp. 2436-2446, 1981.

(Continued)

*Primary Examiner* — Ganapathirama Raghu
(74) *Attorney, Agent, or Firm* — McDermott Will & Emery LLP

(57) ABSTRACT

The present invention provides a method for producing a carotenoid, which comprises culturing a carotenoid-producing bacterium in an amino acid-supplemented medium, and collecting the carotenoid from the resulting cultured product, wherein the amino acid is at least one selected, from the group consisting of glutamic acid, aspartic acid, glutamine, asparagine, alanine, glycine, serine, threonine, arginine, tyrosine, proline, phenylalanine and leucine, and salts thereof.

2 Claims, No Drawings

(56) References Cited

FOREIGN PATENT DOCUMENTS

| WO | 0196591 A1 | 12/2001 |
|---|---|---|
| WO | 2005/118812 A1 | 12/2005 |

OTHER PUBLICATIONS

A. Tsubokura, et al., *Paracoccus carotinifaciens* sp. nov., a new aerobic Gram-negative astaxanthin-producing bacterium, International Journal of Systematic Bacteriology, vol. 49, pp. 277-282, 1999.

J. H. Lee, et al., *Paracoccus haeundaensis* sp. nov., a Gram-negative, halophilic, astaxanthin-producing bacterium, International Journal of Systematic and Evolutionary Microbiology, vol. 54, pp. 1699-1702, 2004.

A. Berry, et al., *Paracoccus zeaxanthinifaciens* sp. nov., a zeaxanthin-producing bacterium, International Journal of Systematic and Evolutionary Microbiology, vol. 53, pp. 231-238, 2003.

An Examination Report, issued on May 30, 2011, in New Zealand Application No. 592213, which corresponds to the present application.

A Supplementary European Search Report mailed Dec. 19, 2012, which issued during the prosecution of European Application No. 09 82 0647.7, which corresponds to the present application.

Mel'nikov, S.S. et al., "The effect of organic compounds on *Spirulina platensis* productivity and the carotenoid content" 1997, Database Biosis Biosciences Information Service, XP002688222.

An Office Action, mailed Dec. 3, 2012, which issued during the prosecution of Chinese Application No. 200980140867.4, which corresponds to the present application.

An Office Action, mailed Oct. 29, 2013, which issued during the prosecution of Japanese Application No. 2010-533939, which corresponds to the present application.

An Extended European Search Report, mailed Dec. 10, 2012, which issued during the prosecution of European Patent Application No. 10735865.7, which corresponds to the present application.

Accession AAT 15842. Aug. 15, 1996.

An Office Action, mailed Sep. 24, 2013, which issued during the prosecution of U.S. Appl. No. 13/146,724, which is related to the present application.

Office Action mailed Jul. 8, 2014, which issued during the prosecution of Japanese Patent Application No. 2010-533939, which corresponds to the present application.

K. S. Lusby et al., Condensed Molasses Solubles and Corn Steep Liquor as Protein Spplements for Range Cows, Oklahoma Agricultural Experiment Station, 1982, pp. 40-46.

Notice of Allowance, mailed Mar. 17, 2014, which issued during the prosecution of U.S Appl. No. 13/146,724, which is related to the present application.

* cited by examiner

CAROTENOID FERMENTATION METHOD

CROSS REFERENCE TO PRIOR APPLICATIONS

This application is a U.S. National Phase application under 35 U.S.C. §371 of International Application No. PCT/JP2009/067935, filed on Oct. 16, 2009 and claims benefit of priority to Japanese Patent Application No. 2008-268106, filed on Oct. 17, 2008. The International Application was published in Japanese on Apr. 22, 2010 as WO 2010/044469 A1 under PCT Article 21(2). All of these applications are herein incorporated by reference.

TECHNICAL FIELD

The present invention relates to a method for microbiological production of carotenoids. More specifically, the present invention relates to a method for microbial fermentation-based production of carotenoids such as astaxanthin, canthaxanthin, zeaxanthin, β-cryptoxanthin, lycopene, β-carotene, phoenicoxanthin, adonixanthin, echinerione, asteroidenone and 3-hydroxyechinenone.

BACKGROUND ART

Carotenoids are natural pigments useful as feed additives, food additives, pharmaceutical ingredients and so on. Carotenoids include astaxanthin, canthaxanthin, zeaxanthin, β-cryptoxanthin, lycopene, β-carotene, phoenicoxanthin, adonixanthin, echinenone, asteroidenone and 3-hydroxyechinenone. Among them, astaxanthin is useful as a body color improver for cultured fish including salmon, trout and red sea bream and/or useful as a feed additive such as a color improver for poultry egg yolk. Astaxanthin is also industrially valuable as a safe and natural food additive or health food material. As in the case of astaxanthin, adonixanthin and phoenicoxanthin are also expected for use as feed additives, food additives, pharmaceutical ingredients or the like once their industrial production has been established. In addition, β-carotene is used as a feed additive, a food additive, a pharmaceutical ingredient or the like, canthaxanthin is used as a feed additive, a food additive, a cosmetic ingredient or the like, and zeaxanthin is used as a food additive, a feed additive or the like. Further, lycopene, echinenone, β-cryptoxanthin, 3-hydroxyechinenone, asteroidenone and others are also expected for use as feed additives, food materials or the like. For production of these carotenoids, chemical synthesis, extraction from natural products, microbial production or other techniques are known.

For chemical synthesis of astaxanthin, conversion from β-carotene (Non-patent Document 1: Pure Appl. Chem., 57, 741, 1985) and synthesis from C15 phosphonium salt (Non-patent Document 2: Helv. Chim. Acta, 64, 2436, 1981) are known. Astaxanthin produced by these chemical synthesis techniques is commercially available as a feed additive. Astaxanthin can also be extracted from fish (e.g., red sea bream, salmon) and crustaceans (e.g., shrimp, crab, krill) because astaxanthin is found in these organisms.

For microbial production of astaxanthin, there are reports of culture in green algae *Haematococcus pluvialis* (Patent Document 1: JP 2007-97584 A), fermentation in red yeast *Phaffia rhodozyma* (Patent Document 2: JP H11-69969 A), and fermentation in bacteria belonging to the genus *Paracoccus* (hereinafter also referred to as "*Paracoccus* sp."). Examples of astaxanthin-producing bacteria belonging to the genus *Paracoccus* include strains E-396 and A-581-1 (Patent Document 3: JP H7-79796 A and Non-patent Document 3: International Journal of Systematic Bacteriology (1999), 49, 277-282). Other astaxanthin-producing bacteria belonging to the genus *Paracoccus* include *Paracoccus marcusii* strain MH1 (Patent Document 4: JP 2001-512030 A), *Paracoccus haeundaensis* strain BC74171 (Non-patent Document 4: International Journal of Systematic and Evolutionary Microbiology (2004), 54, 1699-1702). *Paracoccus* sp. strain N-81106 (Patent Document 5: JP 2007-244205 A), *Paracoccus zeaxanthinifaciens* (Non-patent Document 5: International Journal of Systematic and Evolutionary Microbiology (2003), 53, 231-238) and *Paracoccus* sp. strain PC-1 (Patent Document 6: WO 2005/118812), etc.

However, the above techniques for carotenoid production have some problems. For example, chemical synthesis would make an unfavorable impression on consumers in terms of safety. Likewise, extraction from natural products requires high production costs. Moreover, production in green algae or yeast not only provides low productivity, but also makes difficult carotenoid extraction because of their rigid cell walls.

In contrast, bacteria belonging to the genus *Paracoccus* are advantageous, e.g., in having high growth rate and in achieving high productivity and easy extraction of carotenoids, and some reports have been issued for methods of their culture. JP 2007-143492 A (Patent Document 7) discloses a method in which an iron salt is added during culture, while JP 2008-167665 A (Patent Document 8) discloses a method in which the carbon source concentration is limited. However, these methods are not practical for commercial or industrial purposes because an expensive yeast extract is used in a large amount as a material of the medium.

RELATED ART DOCUMENTS

Patent Documents
[Patent Document 1] JP 2007-97584 A
[Patent Document 2] JP H11-69969 A
[Patent Document 3] JP H7-79796 A
[Patent Document 4] JP 2001-512030 A
[Patent Document 5] JP 2007-244205 A
[Patent Document 6] WO2005/118812
[Patent Document 7] JP 2007-143492 A
[Patent Document 8] JP 2008-167665 A
Non-Patent Documents
[Non-patent Document 1] Pure Appl. Chem., 57, 741, 1985
[Non-patent Document 2] Helv. Chim. Acta, 64, 2436, 1981
[Non-patent Document 3] International Journal of Systematic Bacteriology (1999), 49, 277-282
[Non-patent Document 4] International Journal of Systematic and Evolutionary Microbiology (2004), 54, 1699-1702
[Non-patent Document 5] International Journal of Systematic and Evolutionary Microbiology (2003), 53, 231-238

GENERAL DESCRIPTIONS OF THE INVENTION

Problems to be Solved by the Invention

The present invention has been made under these circumstances and aims to provide a method for microbiological production of carotenoids in high yields and at low costs.

Means for Solving the Problems

As a result of various efforts made to solve the problems stated above, the inventors of the present invention have found that it is possible to improve the productivity of carotenoids when a medium commonly used for bacterial culture is further supplemented with an amino acid or a salt thereof (e.g., sodium glutamate) in the culture of carotenoid-producing bacteria. This finding led to the completion of the present invention.

Namely, the present invention relates to a method for producing a carotenoid, which comprises culturing a carotenoid-producing bacterium in an amino acid-supplemented medium, and collecting the carotenoid from the resulting cultured product, wherein the amino acid is at least one selected from the group consisting of glutamic acid, aspartic acid, glutamine, asparagine, alanine, glycine, serine, threonine, arginine, tyrosine, proline, phenylalanine and leucine, and salts thereof.

In the above method, a preferred amino acid is glutamic acid or a glutamate salt.

The supplemented amino acid concentration may be, for example, 1 mmol/L to 200 mmol/L. As used herein, the term "supplemented amino acid concentration" is intended to mean the amino acid concentration achieved in the medium in which the amino acid is supplemented (i.e., the concentration of supplemented amino acid(s) in the medium).

The carotenoid may be, for example, at least one selected from the group consisting of astaxanthin, canthaxanthin, zeaxanthin, β-cryptoxanthin, lycopene, β-carotene, phoenicoxanthin, adonixanthin, echinenone, asteroidenone and 3-hydroxyechinenone.

In the above method, bacteria preferred for use are those belonging to the genus *Paracoccus*. Such bacteria may also be those having a homology of 95% or more in the base sequence of DNA corresponding to 16S ribosomal RNA with respect to the base sequence represented by SEQ ID NO: 1. In particular, strain E-396 (FERM BF-4283) or A-581-1 (FERM BP-4671) or a mutant thereof is preferred for use.

Effect of the Invention

The present invention enables more efficient production of carotenoids at high concentrations. The present invention also enables microbiological production of carotenoids at low costs.

MODES FOR CARRYING OUT THE INVENTION

The present invention will be further described in more detail below. The scope of the present invention is not limited to the following description, and may be carried out in appropriate modifications other than the following illustrative embodiments without departing from the spirit of the present invention.

All the publications cited herein, for example, the related art documents, laid-open patent publications, patent publications, and other patent-related documents, are incorporated herein in their entirety for reference. The specification of Japanese Patent Application No. 2008-268106, upon which the present application claims the benefit of priority, is incorporated herein.

The present invention relates to a method for producing a carotenoid by culturing a carotenoid-producing bacterium. This method is characterized by that the medium is supplemented with a specific amino acid(s). The method of the present invention allows more efficient and low-cost production of carotenoids at high concentrations.

Although bacteria used in the present invention are not limited in any way as long as they are carotenoid-producing bacteria, preferred for use are bacteria belonging to the genus *Paracoccus*. Among such bacteria belonging to the genus *Paracoccus*, preferred for use are *Paracoccus carotinifaciens*, *Paracoccus marcusii*, *Paracoccus haeundaensis* and *Paracoccus zeaxanthinifaciens*, especially *Paracoccus carotinifaciens*. Specific exemplary strains of bacteria belonging to the genus *Paracoccus* include *Paracoccus carotinifaciens* strain E-396 and *Paracoccus* sp. strain A-581-1 (FERM BP-4671), which are also preferred for use in the present invention.

Other carotenoid-producing bacteria preferred for use are those having high homology in the base sequence of DNA corresponding to 16S ribosomal RNA with respect to the base sequence of the strain E-396 represented by SEQ ID NO: 1. As used herein, the phrase "having high homology" is, for example, intended to mean that there is a homology of preferably 95% or more, more preferably 96% or more, even more preferably 97% or more, particularly preferably 98% or more, most preferably 99% or more between the base sequence represented by SEQ ID NO: 1 and the corresponding base sequences of bacteria to be compared.

The base sequence of DNA corresponding to 16S ribosomal RNA refers to a base sequence having T (thymine) instead of U (uracil) in the base sequence of 16S ribosomal RNA.

Microbial classification based on homology of the base sequence of this 16S ribosomal RNA has become mainstream in recent years. Conventional microbial classifications are based on microbiological properties of microorganisms, such as auxotrophy, sugar assimilation property, etc., and may cause misclassification of microorganisms in some cases when a spontaneous mutation has induced a phenotypic change or the like. In contrast, the base sequence of 16S ribosomal RNA is very stable inheritantly; and hence classification based on the homology of this sequence ensures remarkably improved confidence in classification results when compared to conventional classifications.

The base sequence of 16S ribosomal RNA in *Paracoccus carotinifaciens* strain E-396 has a homology of 99.7%, 99.7%, 99.6%, 99.4%, 95.7% and 95.4% with the base sequences of 16S ribosomal RNA in other carotenoid-producing bacteria, i.e., *Paracoccus marcusii* strain DSM 11574, *Paracoccus* sp. strain N-81106, *Paracoccus haeundaensis* strain BC 741.71, *Paracoccus* sp. strain A-581-1, *Paracoccus zeaxanthinifaciens* strain ATCC 21588 and *Paracoccus* sp. strain PC-1, respectively, which indicates that they are taxonomically very closely related strains. Thus, these strains appear to constitute a group of carotenoid-producing bacteria. For this reason, these strains are preferred for use in the present invention and allow efficient production of carotenoids.

In the present invention, it is also possible to use mutant strains with improved productivity of carotenoids. Examples of improved mutant strains include those having high ability to produce astaxanthin (JP 2001-9.5500 A), those selectively producing canthaxanthin at high levels (JP 2003-304875 A), those selectively producing zeaxanthin and β-cryptoxanthin at high levels (JP 2005-87097 A), and those selectively producing lycopene (JP 2005-87100 A).

Such mutant strains with improved productivity of carotenoids can be obtained by mutagenesis and screening. Any technique may be used for mutagenesis as long as it induces a mutation(s). For example, it is possible to use chemical techniques using a mutagen such as N-methyl-N'-nitro-N-nitrosoguanidine (NTG) or ethylmethane sulfonate (EMS), physical techniques such as ultraviolet irradiation or X-ray irradiation, or biological techniques using gene recombination or transposons, etc. Although bacteria to be mutated are not limited in any way, they are preferably carotenoid-producing bacteria. Alternatively, such mutant strains may be generated as a result of spontaneous mutation.

Any technique may be used for screening of mutant strains, including selection of a desired mutant strain on the basis of colony color on agar medium, as well as selection of a desired mutant strain by carotenoid pigment analysis using absorbance, high performance liquid chromatography, thin-layer chromatography or the like from among mutant strains cultured in test tubes, flasks, fermentation tanks, etc.

Such mutagenesis and screening steps may be performed once, or alternatively, may be repeated twice or more, for example, such that a mutant strain obtained by mutagenesis and screening is subjected to further mutagenesis and screening to obtain a mutant strain with improved productivity.

The strain E-396 listed as an example of carotenoid-producing bacteria used in the present invention has been internationally deposited to the International Patent Organism Depositary, National Institute of Advanced Industrial Science and Technology, as shown below.

International Deposition Authority: International Patent Organism Depositary, National Institute of Advanced Industrial Science and Technology (former National Institute of Bioscience and Human-Technology, Agency of Science and Technology, Ministry of International Trade and Industry), Chuoh 6, Higashi 1-1-1, Tsukuba-shi, Ibaraki-ken, 305-8566

Identification No.: E-396
Deposition No.: FERM BP-4283
Date of original deposition: Apr. 27, 1993

Likewise, the strain A-581-1 listed as another example of carotenoid-producing bacteria used in the present invention has been internationally deposited to the above depositary, as shown below.

Identification No.: A-581-1
Deposition No.: FERM BP-4671
Date of original deposition: May 20, 1994

In the present invention, when cultured in a medium supplemented with a specific amino acid(s), the above carotenoid-producing bacteria can produce larger amounts of carotenoids at higher concentrations than in a medium not supplemented with the amino acid(s).

Carotenoids produced by the method of the present invention are not limited in any way. Examples include astaxanthin, canthaxanthin, zeaxanthin, β-cryptoxanthin, lycopene, β-carotene, phoenicoxanthin, adonixanthin, echinenone, asteroidenone or 3-hydroxyechinenone, Preferred is astaxanthin, canthaxanthin, zeaxanthin or β-cryptozanthin, and more preferred is astaxanthin, zeaxanthin or β-cryptoxanthin. These carotenoids may be produced, either alone or in combination, in the present invention.

The method for culturing the above bacteria in the present invention will be described below.

For culture in the present invention, any medium for carotenoid production may be used, without limitation, as long as it is an amino acid-supplemented medium containing a specific amino acid(s) and allows carotenoid-producing bacteria to grow and produce carotenoids. Preferred for use is a medium containing a carbon source, a nitrogen source, inorganic salts and optionally vitamins, etc. Namely, in the present invention, an amino acid(s) may be added to any medium (e,g., standard medium for carotenoid production) in which carotenoid-producing bacteria can grow and produce carotenoids.

Examples of a carbon source include sugars such as glucose, sucrose, lactose, fructose, trehalose, mannose, mannitol and maltose; organic acids such as acetic acid, fumaric acid, citric acid, propionic acid, malic acid, malonic acid and pyruvic acid; alcohols such as ethanol, propanol, butanol, pentanol, hexanol, isobutanol and glycerol; as well as fats and oils such as soybean oil, rice bran oil, olive oil, corn oil, sesame oil and linseed oil. Among them, glucose or sucrose is preferred for use. One or more of these carbon sources may be used. The amount to be added to the medium before culture (initial medium) will vary depending on the type of carbon source and may be adjusted as appropriate. It is usually 1 to 100 g, preferably 2 to 50 g per liter of the medium. Moreover, such carbon sources are not only added to the initial medium, but also may preferably be supplied, sequentially or continuously during culture.

Examples of an inorganic nitrogen source include ammonium salts (e.g., ammonium nitrate, ammonium sulfate, ammonium chloride, ammonium phosphate), nitrate salts potassium nitrate), ammonia and urea, which may be used either alone or in combination. The amount to be added will vary depending on the type of nitrogen source and may be adjusted as appropriate. It is usually 0.1 g to 20 g, preferably 0.2 to 10 g per liter of the medium.

Examples of an organic nitrogen source include corn steep liquor (including filtered corn steep liquor), Pharmamedia, soybean meal, soybean powder, peanut meal, distiller's solubles and dry yeast, which may be used either alone or in combination. The concentration to be added will vary depending on the type of nitrogen source and may be adjusted as appropriate. It is usually 0 to 80 g/L, preferably 0 to 30 g/L, Such inorganic and organic nitrogen sources are normally added to the initial medium, and may also preferably be supplied sequentially or continuously during culture.

Examples of inorganic salts include phosphate salts (e.g., potassium dihydrogen phosphate, dipotassium hydrogen phosphate, disodium hydrogen phosphate), magnesium salts (e.g., magnesium sulfate, magnesium chloride), iron salts (e.g., iron sulfate, iron chloride), calcium salts (e.g., calcium chloride, calcium carbonate), sodium salts (e.g., sodium carbonate, sodium chloride), manganese salts (e.g., manganese sulfate), cobalt salts (e.g., cobalt chloride), copper salts (e.g., copper sulfate), zinc salts (e.g., zinc sulfate), molybdenum salts (e.g., sodium molybdate), nickel salts (e.g., nickel sulfate), selenium salts sodium selenate), boric acid and potassium iodide, which may be used either alone or in combination. The amount to be added will vary depending on the type of inorganic salt and may be adjusted as appropriate. It is usually 0.0001 to 15 g per liter of the medium. A preferred concentration is 0.02 to 15 g/L, for phosphate salts, magnesium salts, calcium salts, sodium salts and iron salts, and 0.1 to 15 mg/L, for manganese salts, cobalt salts, copper salts, zinc salts, molybdenum salts, nickel salts, selenium salts, boric acid, potassium iodide and so on. Such inorganic salts are normally added to the initial medium, and may also be supplied sequentially or continuously during culture.

Examples of vitamins available for use include cyanocobalamin, riboflavin, pantothenic acid, pyridoxine, thiamine, ascorbic acid, folic acid, niacin, p-aminobenzoic acid, biotin, inositol, choline and the like. The ratio to be added will vary depending on the type of vitamin and may be adjusted as appropriate. It is usually 0.001 to 1000 mg, preferably 0.01 to 100 mg per liter of the medium. Such vitamins are normally added to the initial medium, and may also be supplied sequentially or continuously during culture.

The present invention is characterized by that carotenoid-producing bacteria are cultured in an amino acid-supplemented medium for carotenoid production supplemented with an amino acid(s). When cultured in such an amino acid-supplemented medium for carotenoid production, carotenoid-producing bacteria can produce larger amounts of carotenoids at higher concentrations than in a medium not supplemented with the amino acid(s).

Amino acids used in the present invention are pure products (single products) purified to some extent, i.e., isolated products, but not amino acids contained in naturally occurring mixtures of complex composition (e.g., casamino acid, yeast extract, peptone). Naturally occurring mixtures may contain not only effective amino acids, but also unwanted or inhibitory components, and may further have lot-to-lot variation in their composition. Moreover, naturally occurring mixtures such as casamino acid, yeast extract and peptone are expensive and thus less valuable for industrial use.

Purified amino acids preferably have a purity of 90% or more, more preferably 95% or more, even more preferably 98% or more, particularly preferably 99% or more, It should be noted that amino acids used in the present invention may further comprise other non-amino acid components to the extent not to inhibit the growth of carotenoid-producing bacteria or to the extent not to inhibit carotenoid production by carotenoid-producing bacteria. Although amino acids used for this purpose are preferably, for example, pure amino acids free from other components including impurities, unpurified amino acids (e.g., amino acids with a purity of less than 90%) may also be used as long as they do not inhibit carotenoid production.

As amino acids added to the medium for carotenoid production, glutamic acid, aspartic acid, glutamine, asparagine, alanine, glycine, serine, threonine, arginine, tyrosine, proline, phenylalanine and leucine or salts thereof are preferably used. These amino acids are preferably in the L-form, but may also be a mixture of L- and D-forms. More preferred are glutamic acid, aspartic acid, glutamine and asparagine or salts thereof and even more preferred are glutamic acid and aspartic acid or salts thereof Among them, glutamic acid or a salt thereof is preferred because of its high effect on carotenoid production. Sodium L-glutamate or a hydrate thereof is inexpensive and thus particularly preferred for use, Examples of salts with acids include inorganic acid salts such as hydrochloride salt, hydrobromide salt, sulfate salt and phosphate salt, as well as organic acid salts such as salts with formic acid, acetic acid or lactic acid. Likewise, examples of salts with bases include alkali metal salts (e.g., sodium salt, potassium salt), alkaline earth metal salts (e.g., calcium salt, magnesium salt), organic base salts (e.g., salts with trimethylamine, triethylamine or pyridine), and ammonium salt.

Amino acids added to the medium for carotenoid production are at least one or more of the above amino acids. Although a single amino acid may be used, it is also possible to add two or more amino acids.

Among essential amino acids, cysteine, lysine, isoleucine and methionine have an inhibitory effect on carotenoid production. In the present invention, it is therefore preferred that amino acids except for these amino acids are added to the medium.

Although amino acids are normally added to the initial medium, they may be added intermittently or continuously during culture. Alternatively, amino acids may be added to the initial medium and further added intermittently or continuously during culture.

In the method of the present invention, there is no lower limit for the supplemented amino acid concentration (i.e., the concentration of supplemented amino acids in the medium), but it is preferably 1 mmol/L or more, more preferably 3 mmol/L or more, even more preferably 5 mmol/L or more, particularly preferably 10 mmol/L, and most preferably 15 mmol/L or more. Likewise, there is no upper limit for the supplemented amino acid concentration, but it is preferably 200 mmol/L or less, more preferably 150 mmol/L or less, even more preferably 100 mmol/L or less, even still more preferably 80 mmol/L or less, particularly preferably 60 mmol/L or less, and most preferably 50 mmol/L or less. Thus, in the present invention, the supplemented amino acid concentration is 1 mmol/L to 200 mmol/L, by way of example.

In the present invention, a defoaming agent may preferably be used to suppress bubbling of the culture solution. Such a defoaming agent may be of any type, without limitation, as long as it has the effect of suppressing bubble formation or breaking the bubbles formed and has low inhibitory effect on the producing bacteria. Examples include alcohol-based defoaming agents, polyether-based defoaming agents, ester-based &foaming agents, fatty acid-based defoaming agents, silicon-based defoaming agents, sulfonate-based defoaming agents and so on. The amount to be added will vary depending on the type of defoaming agent and may be adjusted as appropriate. It is usually 0.01 g to 10 g per liter of the medium.

Such a defoaming agent is normally added to the initial medium before sterilization, and may further be added continuously or intermittently during culture. For addition during culture, such a defoaming agent may be automatically added upon detection of bubbles with a sensor, or may be added at given time intervals with a programmed timer, or may be added in response to the growth rate in admixture with, e.g., a carbon source, a nitrogen source or a pH adjustor to be fed, by way of example. The defoaming agent added to the initial medium and the defoaming agent added to the culture solution during culture may be either of the same or different type, depending on the intended effect.

In the present invention, the amino acid-supplemented medium which is supplemented with amino acid(s) is adjusted to have an initial pH of 2 to 12, preferably 6 to 9, more preferably 6.5 to 8.0. It is desirable to also maintain the pH within the above range during culture. Examples of a pH adjustor include aqueous sodium hydroxide, aqueous potassium hydroxide, aqueous sodium carbonate, aqueous ammonia, ammonia gas, aqueous sulfuric acid or mixtures thereof.

In the present invention, the amino acid-supplemented medium is sterilized before use and used for bacterial culture. Sterilization may be accomplished as appropriate by those skilled in the art. For example, the medium in an appropriate vessel may be sterilized by heating in an autoclave. Alternatively, the medium may be sterilized by filtration through a sterile filter.

In the present invention, carotenoid-producing bacteria are inoculated into the amino acid-supplemented medium thus prepared and cultured under given conditions. Inoculation may be accomplished as follows: strains are grown as appropriate by seed culture in such as test tubes, flasks or fermentation tanks and the resulting cultured products are each added to the amino acid-supplemented medium for carotenoid production. Any medium, without limitation, either with or without specific amino acids, may be used for seed culture as long as it ensures good growth of carotenoid-producing bacteria.

Culture is performed in an appropriate culture vessel. Such a culture vessel may be selected as appropriate depending on the culture volume and is exemplified by test tubes, flasks, fermentation tanks and so on.

The culture temperature is set to 15° C. to 80° C., preferably 20° C. to 35° C., more preferably 25° C. to 32° C., and culture is performed under aerobic conditions for usually 1 to 20 days, preferably 2 to 12 days, more preferably 3 to 9 days. Culture under aerobic conditions includes, for example, shaking culture or aeration agitation culture, during which the dissolved oxygen concentration is preferably controlled within a certain range. Control of the dissolved oxygen concentration may be accomplished, for example, by varying the number of agitation rotations, the aeration volume, the internal pressure, etc. The dissolved oxygen concentration is controlled to preferably 0.3 to 1.0 ppm, more preferably 0.5 to 7 ppm, and even more preferably 1 to 5 ppm.

In the present invention, carotenoids in the cultured product obtained by culturing carotenoid-producing bacterial cells or carotenoids collected from the cultured product after some purification procedure can be quantified by high performance liquid chromatography.

Carotenoid-producing bacterial cells can be cultured as described above and carotenoids can be collected from the resulting cultured product.

Such a cultured product may be, for example, a culture solution, a culture supernatant, a concentrated microbial cell solution, wet microbial cells, dry microbial cells, a microbial cell lysate, etc. A culture supernatant may be prepared from a culture solution by centrifugation or filtration to remove microbial cells from the culture solution. A concentrated microbial cell solution may be obtained from a culture solution upon concentration by centrifugation or membrane filtration. Wet microbial cells may be obtained from a culture solution by centrifugation or filtration. Dry microbial cells may be obtained from wet microbial cells or a concentrated microbial cell solution upon drying in a standard manner. The carotenoid-containing dry microbial cells thus obtained may be used directly as feed additives.

In the present invention, any technique may be used, without limitation, to collect carotenoids from the above cultured product as long as it allows stable and efficient collection of carotenoids. Such a technique may be selected as appropriate front extraction and purification techniques known to those skilled in the art.

Prior to carotenoid extraction from the cultured product, the cultured product may be subjected to one or more treatments selected from chemical treatments with alkaline reagents, surfactants or the like, biochemical treatments with lytic enzymes, lipolytic enzymes, proteolytic enzymes or the like, or physical treatments such as ultrasonication or homogenization.

For example, when carotenoids are extracted from the cultured product, any solvent may be used, without limitation, for extraction and washing, including lower alcohols (e.g., methanol, ethanol, isopropanol), acetone, tetrahydrofuran, methylethyl ketone, methylisobutyl ketone, dichloromethane, chloroform, dimethylformamide, dimethyl sulfoxide and so on.

To minimize oxidation of carotenoids during the extraction step, the cultured product may be treated inert gas atmosphere such as nitrogen gas. Moreover, an antioxidant used in pharmaceutical preparations or food products may also be selected and added to the extraction solvent. Alternatively, these treatments may be used in combination, in addition, to minimize light-induced degradation of carotenoids, the cultured product may be treated under light shielding conditions.

The extract thus obtained may be used directly as a carotenoid fraction or may farther be purified before use.

Any technique may be used, without limitation, to separate bacterial cells or others from the extract after the extraction step. Examples include membrane filtration, centrifugation, decantation, etc.

To obtain carotenoid precipitates from the extract, techniques commonly used for this purpose include concentration under heating and/or reduced pressure, as well as crystallization. Alternatively, carotenoid pigments may also he separated, without being concentrated, by precipitation at low temperature or by precipitation with acid and/or alkaline agents or with various salts.

For industrial purposes, crystallization is desired.

The resulting carotenoid precipitates may optionally be suspended and stirred using a small volume of a solvent (e.g., lower alcohol) for washing purposes.

Washing procedures are not limited in any way, and practically preferred procedures include those in which the precipitates are collected by filtration after being suspended and stirred, or those in which a solution is passed from above the precipitates.

The cultured product, extract or purified product obtained as described above may be used as a carotenoid fraction, either alone or in admixture at any ratio.

EXAMPLES

The present invention will be further described in more detail by way of the following illustrative examples. The scope of the present invention is not limited, to the following examples.

In the examples, carotenoids were quantified by high performance liquid chromatography (HPLC) as follows.

Two columns of Wakosil-II 5 SIL-100 ($\phi 4.6 \times 250$ mm) (Wako Pure Chemical Industries, Ltd., Japan) were connected to each other for use as a column. Elution was performed by flowing an n-hexane-tetrahydrofuran-methanol mixed solution (40:20:1), which was a mobile phase, at a flow rate of 1.0 mL/minute at a constant temperature around room temperature. The measurement was performed as follows. Samples were each dissolved in tetrahydrofuran and then diluted 100-fold with the mobile phase. Each dilution was injected in a volume of 20 µL. The column eluate was detected at a wavelength of 470 nm. As a reference for quantification, astaxanthin (SIGMA, Cat. No. A9335) was used. The astaxanthin concentration of the reference solution was determined using the following equation after measuring the absorbance (A) of the reference solution at 477 nm and the area percentage % (B) of the astaxanthin peak at the time of HPLC analysis under the above conditions.

$$\text{Astaxanthin concentration (mg/L)}=A/2150 \times B \times 100$$

Example 1

A medium of the following composition (sucrose 30 g/L, corn steep liquor 30 g/L, potassium dihydrogenphosphate 1.5 g/L, disodium hydrogenphosphate 12-hydrate 3.8 g/L, calcium chloride dihydrate 5.0 g/L, magnesium sulfate 7-hydrate 0.7 g/L, iron sulfate 7-hydrate 0.3 g/L, pH 7.2) was dispensed in 8 ml volumes into cotton-plugged test tubes having an inner diameter of 18 mm and sterilized in an autoclave at 121° C. for 15 minutes to prepare a test tube medium for seed culture.

Next, a medium of the following composition (glucose 30 g/L, filtered corn steep liquor 5 g/L, ammonium sulfate 1.5 g/L, potassium dihydrogenphosphate 1.5 g/L, disodium hydrogenphosphate 12-hydrate 3.8 g/L, calcium chloride dihydrate 5.0 g/L, magnesium sulfate 7-hydrate 0.7 g/L, iron sulfate 7-hydrate 0.6 g/L, ester-based defoaming agent 0.2 g/L) was dispensed in 8 ml volumes into cotton-plugged test tubes having an inner diameter of 18 mm (21 tubes in total).

The mediums in these test tubes were supplemented with 20 amino acids, glycine, alanine, valine, leucine, isoleucine, serine, threonine, aspartic acid, glutamic acid, asparagine, glutamine, lysine, arginine, cysteine, methionine, phenylalanine, tyrosine, tryptophan, histidine and proline, respectively, at 1.0 g/L. One of the tubes was supplemented with no amino acid as a control. Finally, the mediums in the tubes were adjusted to pH 7.1 with aqueous sodium hydroxide or aqueous sulfuric acid and then sterilized in an autoclave at 121° C. for 20 minutes.

*Paracoccus carotinifaciens* strain E-396 (FERM BP-4283) was inoculated into the test tube medium for seed culture and then cultured with shaking at 28° C. for 2 days at 300 spm. The resulting culture solution was then inoculated in 0.1 ml volumes into the 21 test tube media, respectively, and cultured with shaking at 28° C. for 4 days at 300 spm.

Each culture solution was measured for its carotenoid concentration by HPLC and microbial cell growth was determined by OD610 (absorbance at 610 nm). As shown in Table 1, glutamic acid, aspartic acid, glutamine, asparagine, alanine, glycine, serine, threonine, arginine, tyrosine, proline, phenylalanine and leucine were found to have a stimulatory effect on the production of carotenoid pigments. In contrast, cysteine, lysine, isoleucine and methionine were found to have a clear inhibitory effect on carotenoid production.

TABLE 1

| Supplimented component | OD610 | Astaxanthin mg/L | Total carotenoid mg/L |
|---|---|---|---|
| Glycine | 18 | 6.2 | 19.0 |
| Alanine | 13 | 6.2 | 20.3 |
| Valine | 10 | 3.0 | 9.2 |
| Leucine | 11 | 4.7 | 10.1 |
| Isoleucine | 6 | 1.3 | 4.5 |
| Serine | 13 | 6.0 | 16.4 |
| Threonine | 8 | 5.2 | 12.5 |
| Aspartic Acid | 18 | 9.4 | 27.0 |
| Glutamic Acid | 17 | 10.7 | 28.2 |
| Asparagine | 14 | 8.1 | 24.2 |
| Glutamine | 17 | 8.3 | 25.8 |
| Lysine | 11 | 1.1 | 4.9 |
| Arginine | 13 | 5.1 | 11.7 |
| Cysteine | 4 | 0.7 | 3.2 |
| Methionine | 7 | 1.4 | 5.0 |
| Phenylalanine | 10 | 4.9 | 10.6 |
| Tyrosine | 12 | 5.0 | 11.3 |
| Tryptophan | 10 | 3.0 | 7.0 |
| Histidine | 8 | 3.3 | 8.1 |
| Proline | 13 | 5.0 | 10.9 |
| None | 9 | 2.6 | 5.9 |

Example 2

A medium of the following composition (glucose 20 g/L, filtered corn steep liquor 5 g/L, potassium dihydrogenphosphate 0.54 g/L, dipotassium hydrogenphosphate 12-hydrate 2.78 g/L, calcium chloride dihydrate 5.0 g/L, magnesium sulfate 7-hydrate 0.7 g/L, iron sulfate 7-hydrate 3.0 g/L, alcohol-based defoaming agent 0.2 g/L., pH 7.5) was dispensed in 100 ml volumes into 500 mL cotton-plugged Erlenmeyer flasks and sterilized in an autoclave at 121° C. for 15 minutes to prepare a flask medium for seed culture in 8 flasks.

Next, a medium of the following composition (glucose 40 g/L, corn steep liquor 30 g/L, ammonium sulfate 0.5 g/L, potassium dihydrogenphosphate 2.25 g/L, disodium hydrogenphosphate 12-hydrate 5.7 g/L, calcium chloride dihydrate 0.1 g/L, magnesium sulfate 7-hydrate 0.5 g/L, iron sulfate 7-hydrate 5 g/L, alcohol-based defoaming agent 0.5 g/L) was dispensed in 2.0 L volumes into 5 L fermentation tanks (8 tanks in total). To these tanks, monosodium L-glutamate monohydrate was added at 0, 1, 5, 15, 30, 50, 100 and 200 mmol/L, respectively, followed by sterilization in an autoclave at 121° C. for 30 minutes.

A loopful of *Paracoccus carotinifaciens* strain E-396 (FERM BP-4283) was inoculated into the flask medium for seed culture and then cultured with rotary shaking at 29° C. for 2 days at 100 rpm. The resulting culture solution was then inoculated in 80 mL, volumes into the individual fermentation tanks, followed by aerobic culture at 29° C. at an aeration volume of 1 vvm for 100 hours. To maintain a pH of 7.2 during culture, the pH was continuously controlled with 15% aqueous ammonia. Glucose was added in an amount of 30 g on day 1 and day 2 of culture to prevent glucose depletion. In addition, the minimum number of agitation rotations was set to 200 rpm, and the number of agitation rotations was varied such that the dissolved oxygen concentration in the culture solution was maintained at 2 to 4 ppm. Bubbling was detected with a bubble sensor and suppressed by automatic addition of an alcohol-based defoaming agent.

At the completion of culture, each culture solution was measured for its carotenoid concentration by HPLC. The results obtained are as shown in Table 2. All the samples containing glutamic acid at concentrations from 1 to 200 mmol/L were found to show a higher produced carotenoid concentration when compared to the sample without glutamic acid.

TABLE 2

| | Glutamic acid concentration mmol/L | | | | | | | |
|---|---|---|---|---|---|---|---|---|
| | 0 | 1 | 5 | 15 | 30 | 50 | 100 | 200 |
| | Produced carotenoid concentration mg/L | | | | | | | |
| β-Carotene | 3.5 | 4.3 | 6.2 | 5.8 | 5.9 | 4.9 | 5.5 | 4.6 |
| Echinenone | 1.3 | 1.6 | 1.9 | 2.1 | 2.2 | 2.3 | 2.0 | 1.7 |
| 3-Hydroxy-echinenone | 0.2 | 0.2 | 0.3 | 0.3 | 0.3 | 0.4 | 0.3 | 0.3 |
| Canthaxanthin | 1.8 | 2.0 | 3.7 | 3.0 | 3.1 | 2.0 | 2.8 | 2.4 |
| Phoenico-xanthin | 4.4 | 5.1 | 7.8 | 7.2 | 7.4 | 6.4 | 7.0 | 5.9 |
| β-Cryptoxanthin | 0.04 | 0.05 | 0.07 | 0.07 | 0.08 | 0.07 | 0.06 | 0.05 |
| Astaxanthin | 12.9 | 18.3 | 27.3 | 30.8 | 30.3 | 30.9 | 28.6 | 23.5 |
| Asteroidenone | 0.4 | 0.4 | 0.4 | 0.6 | 0.6 | 0.9 | 0.6 | 0.5 |
| Adonixanthin | 5.9 | 7.8 | 7.8 | 9.6 | 9.3 | 10.8 | 9.2 | 7.6 |
| Zeaxanthin | 0.12 | 0.17 | 0.18 | 0.19 | 0.20 | 0.21 | 0.18 | 0.15 |
| Total Carotenoid | 30.6 | 39.9 | 55.7 | 59.7 | 59.4 | 58.9 | 56.2 | 46.7 |

Example 3

*Paracoccus carotinifaciens* strain E-396 was mutated with N-methyl-N'-nitro-N-nitroguanidine to select colonies with darker red color. The selected strains were analyzed for carotenoids in their culture solutions to select a mutant strain Y-1071 with improved astaxanthin productivity.

A medium of the following composition (sucrose 30 g/L, Pharmamedia 30 g/L, potassium dihydrogenphosphate 0.8 g/L, dipotassium hydrogenphosphate 4.2 g/L, calcium chloride dihydrate 1 g/L, magnesium sulfate 7-hydrate 12 g/L, iron sulfate 7-hydrate 1 g/L, pH 7.2) was dispensed in 8 ml volumes into cotton-plugged test tubes having an inner diameter 18 mm and sterilized in an autoclave at 121° C. for 15 minutes to prepare a test tube medium fir seed culture.

Next, a medium of the following composition (sucrose 30 g/L, Pharmamedia 20 g/L, ammonium sulfate 1.5 g/L, potassium dihydrogenphosphate 1.5 g/L, disodium hydrogenphosphate 12-hydrate 3.8 g/L, calcium chloride dihydrate 0.1 g/L, magnesium sulfate 7-hydrate 4.5 g/L, iron sulfate 7-hydrate 5 g/L, biotin 1 mg/L, silicon-based defoaming agent 1 g/L) was dispensed in 8 ml volumes into cotton-plugged test tubes having an inner diameter of 18 mm (2 tubes in total). One of the tubes was supplemented with monosodium L-glutamate monohydrate to 30 mmol/L, while the other was supplemented with nothing as a control. Finally, the mediums in the tubes were adjusted to pH 7.1 with aqueous sodium hydroxide and then sterilized in an autoclave at 121° C. for 20 minutes, The *Paracoccus* sp. strain Y-1071 selected above was inoculated into the test tube medium for seed culture and then cultured with shaking at 28° C. for 2 days at 300 spm. The resulting culture solution was then inoculated in 0.1 ml volumes into the two test tube media and cultured with shaking at 28° C. for 4 days at 300 spm.

Each culture solution was measured for its carotenoid concentration by HPLC. The results obtained are as shown in Table 3.

In the mutant *Paracoccus* sp. strain Y-1071, the sample containing glutamic acid was also found to show a higher produced carotenoid concentration when compared to the sample without glutamic acid.

TABLE 3

| Glutamic acid concentration | | 0 mmol/L | 30 mmol/L |
|---|---|---|---|
| β-Carotene | mg/L | 6.9 | 13.1 |
| Echinenone | mg/L | 3.4 | 6.5 |
| 3-Hydroxyechinenone | mg/L | 0.4 | 0.7 |
| Canthaxanthin | mg/L | 5.5 | 10.0 |
| Phoenicoxanthin | mg/L | 13.6 | 24.8 |
| β-Cryptoxanthin | mg/L | 0.04 | 0.10 |
| Astaxanthin | mg/L | 46.4 | 94.8 |
| Asteroidenone | mg/L | 0.9 | 1.5 |
| Adonixanthin | mg/L | 11.3 | 18.4 |
| Zeaxanthin | mg/L | 0.17 | 0.28 |
| Total Carotenoid | mg/L | 88.7 | 170.2 |

Example 4

A medium of the following composition (glucose 20 g/L, dry yeast 5 g/L, potassium dihydrogenphosphate 1.5 g/L, disodium hydrogenphosphate 12-hydrate 3.8 g/L, calcium chloride dihydrate 0.1 g/L, magnesium sulfate 7-hydrate 0.7 g/L, iron sulfate 7-hydrate 3 g/L, pH 7.2) was dispensed in 8 ml volumes into cotton-plugged test tubes having an inner diameter of 18 mm and sterilized in an autoclave at 121° C. for 15 minutes to prepare a test tube medium for seed culture.

Next, a medium of the following composition (glucose 40 g/L, ammonium sulfate 1.5 g/L, potassium dihydrogenphosphate 0.54 g/L, dipotassium hydrogenphosphate 2,78 g/L, calcium chloride dihydrate 1 g/L, sodium chloride 3 g/L, magnesium sulfate 7-hydrate 0.7 g/L, iron sulfate 7-hydrate 5 g/L, zinc sulfate 7-hydrate 2 mg/L, cobalt chloride 6-hydrate 2 mg/L, copper sulfate 5-hydrate 1 mg/L, manganese sulfate 5-hydrate 4 mg/L, sodium molybdate dihydrate 2 mg/L, nickel sulfate 6-hydrate 1 mg/L, sodium selenate 0.5 mg/L, boric acid 5 mg/L, potassium iodide 1 mg/L, cyanocobalamin 1 mg/L, riboflavin 10 mg/L, calcium pantothenate 15 mg/L, pyridoxine hydrochloride salt 20 mg/L, thiamine hydrochloride salt 30 mg it, ascorbic acid 30 mg/L, folic acid 1 mg/L, niacin 15 mg/L, p-aminobenzoic acid 10 mg/L, biotin 0.1 mg/L, myo-inositol 50 mg/L, choline 10 mg/L, polyether-based defoaming agent 0.2 g/L) was dispensed in 8 ml volumes into cotton-plugged test tubes having an inner diameter of 18 mm (4 tubes in total).

For use in this medium, glucose, inorganic salts, trace metals and vitamins were prepared separately. Glucose, inorganic salts and trace metals were sterilized by heating at 121° C. for 15 minutes, while vitamins were sterilized by filtration. Then, these 4 solutions were mixed together.

Further, one of the test tubes was supplemented with a heat-sterilized aqueous solution of monosodium L-glutamate monohydrate to 6 g/L (32 mmol/L), another tube was supplemented with a heat-sterilized aqueous yeast extract to 6 g/L, another tube was supplemented with the same yeast extract to 12 g/L, and the other tube was supplemented with nothing. Finally, the mediums in the tubes were aseptically supplemented with 12% aqueous ammonia to give pH 7.2.

The mutant *Paracoccus* sp. strain Y-1071 selected in Example 3 was inoculated into the test tube medium for seed culture and then cultured with shaking at 30° C. for 2 days at 300 spm. The resulting culture solution was then inoculated in 0.1 ml volumes into the 4 test tube media and cultured with shaking at 3(1° C. for 3 days at 300 spm.

Each culture solution was measured for its carotenoid concentration by HPLC. As shown in Table 4, the sample containing glutamic acid was found to show a higher produced carotenoid concentration when compared to the sample without glutamic acid. Neither of the samples containing yeast extract was found to have a significant improving, effect comparable to that of the sample containing glutamic acid.

TABLE 4

| | Produced carotenoid concentration mg/L | | | |
|---|---|---|---|---|
| | Control | Glutamic acid 6 g/L | Yeast extract 6 g/L | Yeast extract 12 g/L |
| β-Carotene | 1.1 | 2.0 | 1.5 | 1.4 |
| Echinenone | 0.5 | 0.9 | 0.7 | 0.5 |
| 3-Hydroxyechinenone | 0.1 | 0.2 | 0.2 | 0.1 |
| Canthaxanthin | 0.9 | 1.8 | 1.4 | 1.2 |
| Phoenicoxanthin | 1.9 | 4.1 | 2.6 | 2.4 |
| β-Cryptoxanthin | 0.01 | 0.02 | 0.01 | 0.01 |
| Astaxanthin | 5.3 | 13.7 | 7.7 | 6.1 |
| Asteroidenone | 0.1 | 0.2 | 0.1 | 0.1 |
| Adonixanthin | 1.4 | 3.3 | 1.7 | 1.6 |
| Zeaxanthin | 0.03 | 0.06 | 0.04 | 0.04 |
| Total Carotenoid | 11.1 | 26.3 | 16.0 | 13.5 |

Example 5

A medium of the following composition (sucrose 20 g/L, filtered corn steep liquor 5 g/L, potassium dihydrogenphosphate 0.54 g/L, dipotassium hydrogenphosphate 12-hydrate 2.78 g/L, calcium chloride dihydrate 5.0 g/L, magnesium sulfate 7-hydrate 0.7 g/L, iron sulfate 7-hydrate 3.0 g/L, alcohol-based &foaming agent 0.2 g/L, pH 7.5) was dispensed in 100 ml volumes into 500 mL cotton-plugged Erlenmeyer flasks and sterilized in an autoclave at 121° C., for 15 minutes to prepare a flask medium for seed culture in 2 flasks.

Next, a medium of the following composition (glucose 40 g/L, corn steep liquor 30 g/L, ammonium sulfate 0.5 g/L, potassium dihydrogenphosphate 2.25 g/L, disodium hydrogenphosphate 12-hydrate 5.7 g/L, calcium chloride dihydrate g/L, magnesium sulfate 7-hydrate 0.5 g/L, iron sulfate 7-hydrate 5 g/L, alcohol-based defoaming agent 0.5 g/L) was dispensed in 2.0 L volumes into 5 L fermentation tanks (2 tanks in total). One of the fermentation tanks was supplemented with monosodium L-glutamate monohydrate to 15 mmol/L, while the other was supplemented with nothing as a control. These fermentation tanks were sterilized in an autoclave at 121° C. for 30 minutes.

A loopful of *Paracoccus* sp. strain A-581-1 (FERM BP-4671) was inoculated into the flask medium for seed culture and then cultured with rotary shaking at 27° C. for 2 days at 150 rpm. The resulting culture solution was then inoculated in 90 mL volumes into the individual fermentation tanks, followed by aerobic culture at 27° C. at an aeration volume of 1 vvm for 100 hours. To maintain a pH of 7.1 during culture, the pH was continuously controlled with 20% aqueous sodium hydroxide. Glucose was added in an amount of 30 g on day and day 2 of culture to prevent glucose depletion. At 22 and 29 hours of culture, monosodium L-glutamate monohydrate and ammonium sulfate were added in amounts of 5 g and 3 g, respectively, per liter of the initial medium. The minimum number of agitation rotations was set to 100 rpm, and the number of agitation rotations was varied such that the dissolved oxygen concentration in the culture solution was maintained at 2 to 4 ppm. An alcohol-based defoaming agent was added in an amount of 0.1 g per hour to prevent bubble formation, At the completion of culture, each culture solution was measured for its carotenoid concentration by HPLC. The results obtained are as shown in Table 5. The sample containing glutamic acid was found to show a higher produced carotenoid concentration when compared to the sample without glutamic acid.

TABLE 5

| Glutamic acid concentration | | 0 mmol/L | 15 mmol/L |
|---|---|---|---|
| β-Carotene | mg/L | 0.92 | 1.76 |
| Echinenone | mg/L | 0.30 | 0.51 |
| 3-Hydroxyechinenone | mg/L | 0.03 | 0.05 |
| Canthaxanthin | mg/L | 0.56 | 1.22 |
| Phoenicoxanthin | mg/L | 1.13 | 2.01 |
| β-Cryptoxanthin | mg/L | 0.00 | 0.01 |
| Astaxanthin | mg/L | 3.13 | 5.97 |
| Asteroidenone | mg/L | 0.01 | 0.02 |
| Adonixanthin | mg/L | 1.55 | 2.10 |
| Zeaxanthin | mg/L | 0.02 | 0.03 |
| Total Carotenoid | mg/L | 7.65 | 13.68 |

Example 6

*Paracoccus* sp. strain A-581-1 (FERM BP-4671) was mutated by ultraviolet irradiation to select colonies with darker red color. The selected strains were analyzed for carotenoids in their culture solutions to select a mutant strain K-185 with improved astaxanthin productivity.

A medium of the following composition (sucrose 30 g/L, corn steep liquor 30 g/L, potassium dihydrogenphosphate 1.5 g/L, disodium hydrogenphosphate 12-hydrate 3.8 g/L, calcium chloride dihydrate 5.0 g/L, magnesium sulfate 7-hydrate 0.7 g/L, iron sulfate 7-hydrate 0.3 g/L, pH 7.2) was dispensed in 8 ml volumes into cotton-plugged test tubes having an inner diameter of 18 mm and sterilized in an autoclave at 121° C. for 15 minutes to prepare a test tube medium for seed culture.

Next, a medium of the following composition (glucose 30 g/L, soybean meal 20 g/L, ammonium sulfate 1.5 g/L, potassium dihydrogenphosphate 1.5 g/L, disodium hydrogenphosphate 12-hydrate 3.8 g/L, calcium chloride dihydrate 5.0 g/L, magnesium sulfate 7-hydrate 0.7 g/L, iron sulfate 7-hydrate 0.6 g/L, ester-based defoaming agent 0.2 g/L) was dispensed in 8 ml volumes into cotton-plugged test tubes having an inner diameter of 18 mm (2 tubes in total). One of the test tubes was supplemented with monosodium L-glutamate monohydrate to 30 mmol/L, while the other was supplemented with nothing as a control. Finally, the mediums in the tubes were adjusted to pH 7.1 with aqueous ammonia and then sterilized in an autoclave at 121° C. for 20 minutes.

The *Paracoccus* sp. strain K-185 was inoculated into the test tube medium for seed culture and then cultured with shaking at 28° C. for 2 days at 300 spm. The resulting culture solution was then inoculated in 0.1. ml volumes into the two test tube mediums and cultured with shaking at 28° C. for 3 days at 300 spm. Each culture solution was measured for its carotenoid concentration by HPLC. The results obtained are as shown in Table 6.

In the mutant *Paracoccus* sp. strain K-185, the sample containing glutamic acid was also fund to show a higher produced carotenoid concentration when compared to the sample without glutamic acid.

TABLE 6

| Glutamic acid concentration | | 0 mmol/L | 30 mmol/L |
|---|---|---|---|
| β-Carotene | mg/L | 1.3 | 2.1 |
| Echinenone | mg/L | 0.4 | 0.6 |
| 3-Hydroxyechinenone | mg/L | 0.1 | 0.1 |
| Canthaxanthin | mg/L | 0.9 | 1.3 |
| Phoenicoxanthin | mg/L | 1.3 | 2.0 |
| β-Cryptoxanthin | mg/L | 0.01 | 0.02 |
| Astaxanthin | mg/L | 5.6 | 9.2 |
| Asteroidenone | mg/L | 0.1 | 0.1 |
| Adonixanthin | mg/L | 1.2 | 1.6 |
| Zeaxanthin | mg/L | 0.02 | 0.03 |
| Total Carotenoid | mg/L | 10.9 | 17.1 |

Example 7

The strain E-396 (FERM BP-4283) was mutated with N-methyl-N'-nitro-N-nitrosoguanidine to select mutant strain colonies with red-purple color. Carotenoid compounds in their culture solutions were further analyzed by high performance liquid chromatography to select a strain L-25 specifically producing lycopene.

A medium of the following composition (sucrose 30 g/L, corn steep liquor 30 g/L, potassium dihydrogenphosphate 1.5 g/L, disodium hydrogenphosphate 12-hydrate 3.8 g/L, calcium chloride dihydrate 5.0 g/L, magnesium sulfate -hydrate 0.7 g/L, iron sulfate 7-hydrate 0.3 g/L, pH 7.2) was dispensed in 8 ml volumes into cotton-plugged test tubes having an inner diameter of 18 mm and sterilized in an autoclave at 121° C. for 15 minutes to prepare a test tube medium for seed culture.

Next, a medium of the following composition (glucose 30 g/L, filtered corn steep liquor 5 g/L, ammonium sulfate 1.5 g/L, potassium dihydrogenphosphate 1.5 g/L, disodium hydrogenphosphate 12-hydrate 3.8 g/L, calcium chloride dihydrate 5.0 g/L, magnesium sulfate 7-hydrate 0.7 g/L, iron sulfate 7-hydrate 0.6 g/L, ester-based defoaming agent 0.2 g/L) was dispensed in 8 ml volumes into cotton-plugged test tubes having an inner diameter of 18 mm (2 tubes in total). One of the test tubes was supplemented with monosodium L-glutamate monohydrate to 30 mmol/L, while the other was supplemented with nothing as a control. Finally, the mediums in the tubes were adjusted to pH 7.1 with aqueous ammonia and then sterilized in an autoclave at 121° C. for 20 minutes.

The *Paracoccus* sp. strain L-25 selected above was inoculated, into the test tube medium for seed culture and then cultured with shaking at 28° C. for 2 days at 300 spin. The resulting culture solution was then inoculated in 0.1 ml volumes into the two test tube mediums and cultured with shaking at 28° C. for 3 days at 300 spm. Each culture solution was measured for its carotenoid concentration by HPLC. The results obtained are as shown in Table 7.

in the mutant *Paracoccus* sp, strain L-25, the sample containing glutamic acid, was also found to show a higher produced carotenoid concentration when compared to the sample without glutamic acid.

TABLE 7

| Glutamic acid concentration | | 0 mmol/L | 30 mmol/L |
|---|---|---|---|
| Lycopene | mg/L | 12.3 | 19.6 |
| Astaxanthin | mg/L | 0.2 | 0.3 |
| Adonixanthin | mg/L | 0.2 | 0.3 |
| Total Carotenoid | mg/L | 12.7 | 20.2 |

Example 8

A medium of the following composition (sucrose 20 g/L, filtered corn steep liquor 5 g/L, potassium dihydrogenphosphate 0.54 g/L, dipotassium hydrogenphosphate 12-hydrate 2.78 g/L, calcium chloride dihydrate 5.0 g/L, magnesium sulfate 7-hydrate 0.7 g/L, iron sulfate 7-hydrate 3.0 g/L, fatty acid-based defoaming agent 0.2 g/L, 7.5) was dispensed in 100 ml volumes into 500 mL cotton-plugged Erlenmeyer flasks and sterilized in an autoclave at 121° C. for 15 minutes to prepare a flask medium for seed culture in 2 flasks, Next, a medium of the following composition (sucrose 40 g/L, corn steep liquor 30 g/L, ammonium sulfate 0.5 g/L, potassium dihydrogenphosphate 2.25 g/L, disodium hydrogenphosphate 12-hydrate 5.7 g/L, calcium chloride dihydrate 0.1 g/L, magnesium sulfate 7-hydrate 0.5 g/L, iron sulfate 7-hydrate 5 g/L, fatty acid-based defoaming agent 0.5 g/L) was dispensed in 2.0 L volumes into 5 L fermentation tanks (2 tanks in total). One of the fermentation tanks was supplemented with monosodium L-glutamate monohydrate to 50 mmol/L, while the other was supplemented with nothing as a control. These fermentation tanks were sterilized in an autoclave at 121° C. for 30 minutes, A loopful of the mutant *Paracoccus* sp, strain Y-1071 selected in Example 3 was inoculated into the flask medium for seed culture and then cultured with rotary shaking at 28° C. for 2 days at 150 rpm. The resulting culture solution was then inoculated in 80 mL volumes into the individual fermentation tanks, followed by aerobic culture at 28° C. at an aeration volume of 1 vvm for 120 hours. To maintain a of 7.2 during culture, the pH was continuously controlled with 15% aqueous ammonia. Glucose was added in an amount of 30 g on day 1, day 2 and day 3 of culture to prevent glucose depletion. The minimum number of agitation rotations was set to 100 rpm, and the number of agitation rotations was varied such that the dissolved oxygen concentration in the culture solution was maintained at 2 to 3 ppm. Bubbling was detected with a bubble sensor and suppressed by automatic addition of a fatty acid-based defoaming agent.

At the completion of culture, each culture solution was measured for its carotenoid concentration by HPLC. The results obtained are as shown in Table 8, The sample containing glutamic acid was found to show a higher produced carotenoid concentration when compared to the sample without glutamic acid.

TABLE 8

| Glutamic acid concentration | | 0 mmol/L | 50 mmol/L |
|---|---|---|---|
| β-Carotene | mg/L | 57 | 93 |
| Echinenone | mg/L | 32 | 62 |
| 3-Hydroxyechinenone | mg/L | 5 | 10 |
| Canthaxanthin | mg/L | 58 | 101 |
| Phoenicoxanthin | mg/L | 131 | 217 |
| β-Cryptoxanthin | mg/L | 0.3 | 0.5 |
| Astaxanthin | mg/L | 376 | 805 |
| Asteroidenone | mg/L | 5 | 9 |
| Adonixanthin | mg/L | 70 | 158 |
| Zeaxanthin | mg/L | 2 | 3 |
| Total Carotenoid | mg/L | 737 | 1458 |

Sequence Listing Free Text

SEQ ID NO: 1: Explanation on unknown organism (E-396) n=a, c, g or t (Location: 1350)

The invention claimed is:

1. A method for producing a carotenoid, which comprises culturing a carotenoid-producing bacterium in an amino acid-supplemented medium, and collecting the carotenoid from the resulting cultured product, wherein the amino acid is at least one selected from the group consisting of glutamic acid and salts thereof, wherein the supplemented amino acid concentration is 5 mmol/L to 100 mmol/L, wherein the carotenoid is astaxanthin, wherein the bacterium belongs to the genus *Paracoccus*, and wherein the bacterium has a homology of 98% or more in the polynucleotide sequence of DNA corresponding to 16S ribosomal RNA with respect to the nucleotide sequence of SEQ ID NO:1, and wherein the bacterium is a mutant that has higher productivity of astaxanthin than its parent.

2. The method according to claim 1, wherein the bacterium is strain E-396 or A-581-1 or a mutant thereof.

* * * * *

SEQUENCE LISTING

```
<160> NUMBER OF SEQ ID NOS: 1

<210> SEQ ID NO 1
<211> LENGTH: 1452
<212> TYPE: DNA
<213> ORGANISM: Unknown
<220> FEATURE:
<223> OTHER INFORMATION: Description of Unknown Organism:E-396
<220> FEATURE:
<221> NAME/KEY: misc_feature
<222> LOCATION: (1350)..(1350)
<223> OTHER INFORMATION: n is a, c, g, or t

<400> SEQUENCE: 1
agtttgatcc tggctcagaa cgaacgctgg cggcaggctt aacacatgca agtcgagcga      60
gaccttcggg tctagcggcg gacgggtgag taacgcgtgg gaacgtgccc ttctctacgg     120
aatagccccg ggaaactggg agtaataccg tatacgccct ttgggggaaa gatttatcgg     180
agaaggatcg gcccgcgttg gattaggtag ttggtggggt aatggcccac caagccgacg     240
atccatagct ggtttgagag gatgatcagc cacactggga ctgagacacg gcccagactc     300
```

-continued

```
ctacgggagg cagcagtggg gaatcttaga caatggggc  aaccctgatc tagccatgcc   360
gcgtgagtga tgaaggcctt agggttgtaa agctctttca gctgggaaga taatgacggt   420
accagcagaa gaagcccgg  ctaactccgt gccagcagcc gcggtaatac ggaggggct    480
agcgttgttc ggaattactg ggcgtaaagc gcacgtaggc ggactggaaa gtcagaggtg   540
aaatcccagg gctcaacctt ggaactgcct ttgaaactat cagtctggag ttcgagagag   600
gtgagtggaa ttccgagtgt agaggtgaaa ttcgtagata ttcggaggaa caccagtggc   660
gaaggcggct cactggctcg atactgacgc tgaggtgcga aagcgtgggg agcaaacagg   720
attagatacc ctggtagtcc acgccgtaaa cgatgaatgc cagacgtcgg caagcatgct   780
tgtcggtgtc acacctaacg gattaagcat tccgcctggg gagtacggtc gcaagattaa   840
aactcaaagg aattgacggg gcccgcaca  agcggtggag catgtggttt aattcgaagc   900
aacgcgcaga accttaccaa cccttgacat ggcaggaccg ctggagagat tcagctttct   960
cgtaagagac ctgcacacag gtgctgcatg gctgtcgtca gctcgtgtcg tgagatgttc   1020
ggttaagtcc ggcaacgagc gcaacccacg tccctagttg ccagcaattc agttgggaac   1080
tctatggaaa ctgccgatga taagtcggag gaaggtgtgg atgacgtcaa gtcctcatgg   1140
gccttacggg ttgggctaca cacgtgctac aatggtggtg acagtgggtt aatcccaaa    1200
agccatctca gttcggattg tcctctgcaa ctcgagggca tgaagttgga atcgctagta   1260
atcgcggaac agcatgccgc ggtgaatacg ttcccgggcc ttgtacacac cgcccgtcac   1320
accatgggag ttggttctac ccgacgacgn tgcgctaacc ttcgggggc  aggcggccac   1380
ggtaggatca gcgactgggg tgaagtcgta acaaggtagc cgtagggaa  cctgcggctg   1440
gatcacctcc tt                                                       1452
```